United States Patent [19]

Speranza et al.

[11] 4,102,866

[45] Jul. 25, 1978

[54] METHOD OF MAKING GLYCIDYL ETHERS OF NOVOLAK RESINS

[75] Inventors: George P. Speranza; Harold G. Waddill, both of Austin, Tex.

[73] Assignee: Texaco Development Corporation, New York, N.Y.

[21] Appl. No.: 736,809

[22] Filed: Oct. 29, 1976

[51] Int. Cl.² .......................................... C08G 59/08
[52] U.S. Cl. .............................. 528/135; 260/348.15; 528/132
[58] Field of Search ............ 260/59 EP, 348.6, 348.15

[56] References Cited

U.S. PATENT DOCUMENTS

| | | | |
|---|---|---|---|
| 2,658,885 | 11/1953 | D'Alelio | 260/53 |
| 2,829,124 | 4/1958 | Napravnik et al. | 260/60 |
| 3,860,561 | 1/1975 | Vargiu et al. | 260/59 EP |

*Primary Examiner*—Harold D. Anderson
*Assistant Examiner*—E. A. Nielsen
*Attorney, Agent, or Firm*—Carl G. Ries; Thomas H. Whaley; James L. Bailey

[57] ABSTRACT

Covers a glycidyl ether composition useful as an epoxy resin which comprises the reaction product of an epihalohydrin and a novolak resin containing 5–25 weight percent of phenol or substituted phenol based on the weight of said novolak resin. Also covers a method of preparing said glycidyl ether composition.

6 Claims, No Drawings

METHOD OF MAKING GLYCIDYL ETHERS OF NOVOLAK RESINS

BACKGROUND OF THE INVENTION

1. Field of the Invention

This invention relates to specific glycidyl ether compositions useful in the preparation of thermo set epoxy resins.

2. Prior Art

Epoxy resins constitute a broad class of polymeric materials having a wide range of physical characteristics. The resins are characterized by epoxide groups which are cured by reaction with certain catalysts or curing agents to provide cured epoxy resin compositions with certain desirable properties. The most commonly used curing agents are aliphatic amines such as diethylenetriamine, triethylenetetramine, ureas, substituted ureas, polyoxyalkylenepolyamines and the like. Such cured epoxy resins are useful as coatings, castings, sealants and adhesives.

One particular class of epoxy resins are those prepared from the glycidyl ethers of novolak resins. We have now found a new class of glycidyl ether compositions of epoxy resins possessing a number of advantages as set out hereinafter.

SUMMARY OF THE INVENTION

Covers glycidyl ether compositions useful as epoxy resins which comprises the reaction product of an epihalohydrin and a novolak resin containing 5–25 weight percent of phenol or substituted phenol based on the weight of said novolak resin.

DESCRIPTION OF THE PREFERRED EMBODIMENTS

To provide the glycidyl ethers of novolak resins and epoxy resins thereof described here, one first prepares a novolak resin. These phenol-aldehyde resins are polynuclear compounds having the structure:

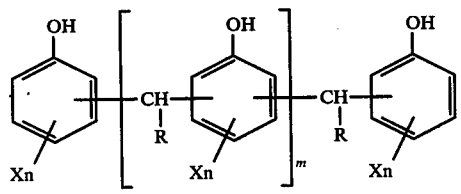

wherein R is hydrogen or an alkyl radical having from 1 to 4 carbon atoms, X is hydrogen, hydroxy, chlorine, bromine or an alkyl radical having from 1 to 12 carbon atoms, $n$ is an integer from 1 to 2 and $m$ is an integer from 0 to 4.

The novolak resins are prepared by condensing phenol or an ortho or para-substituted derivative thereof, such as cresol, xylenol, resorcinol, chlorophenol, bromophenol, isopropylphenol, t-butylphenol, octylphenol, nonylphenol, or dodecylphenol with an aldehyde in acidic solution and at a reaction temperature between about 60 and 160° C. The novolak resins may contain from 2 to 6 aromatic rings per molecule, but preferably contain an average of from 2.2 to 3.2 aromatic preferably, benzene rings.

The aldehydic reactant can be formaldehyde, acetaldehyde, propionaldehyde, or butyraldehyde, but is preferably formaldehyde, or a derivative, e.g. trioxane. Suitable acidic catalysts for the novolak resin reaction are oxalic acid, zinc acetate, hydrochloric acid, sulfuric acid or stannous octoate.

The reaction for making the novolak resins is carried out at the above temperature range and at atmospheric pressure or thereabouts, employing the phenol or phenolic derivative in amounts corresponding to from about 1.5 to about 3.0 moles of phenolic compounds per mole of aldehyde.

In the usual case, in order to utilize a novolak resin as an epoxy resin source, the novolak is first stripped of excess phenolic compound. It has been thought that it is necessary to strip off excess phenol in order to desirably increase the functionality and provide proper crosslinking. One would expect that by leaving present in the resin excess phenolic compound, overall functionality of the resin mixture would be undesirably lowered to give a product of two or lower functionality including mono-functional products, having unsuitable properties as a source for epoxy resin formation or even other uses. However, it has been found that a suitable, and in fact greatly desirable source for epoxies may be prepared directly from a novolak resin containing excess phenol by leaving in the resin the excess of phenol and avoiding a separate stripping step. One thus achieves a considerable cost and time savings particularly in terms of time and energy savings. As a still further advantage, the unstripped novolak resin has a lower viscosity than the conventional stripped novolak resin resulting in easier handling. Lastly, due to the presence of free phenol in the novolak, resultant glycidyl ethers of the novolak formed by reaction of the novolak containing free phenol with epichlorohydrin results in a total composition having a built-in reactive plasticizer in the form of phenol glycidyl ether.

Greatly preferred novolak resins containing excess phenol or phenolic compound are those having a hydroxyl number ranging from about 180 to about 325.

As used above, the hydroxyl number is defined as the number of milligrams of potassium hydroxide required for the complete neutralization of the hydrolysis product of the fully acetylated derivative prepared from one gram of polyol. The hydroxyl number can also be defined by the equation:

$$OH = \frac{56.1 \times 1{,}000 \times f}{MX}$$

where
- OH = hydroxyl number of the polyol
- F = average functionality, that is the average number of hydroxyl groups per molecule of polyol.
- MW = average molecular weight of the polyol.

To prepare the epoxy novolak resins of the invention one then simply reacts the above described novolak resin containing free phenol or substituted phenol with an epihalohydrin such as epichlorohydrin. Through such reaction, one essentially then is preparing a glycidyl ether of a novolak resin which additionally comprises 5–25 percent by weight based on the weight of the glycidyl ether of the novolak resin of a monophenol glycidyl ether. If the reaction with epihalohydrin is carried out in the presence of a basic catalyst, e.g. sodium or potassium hydroxide, a curable epoxy novolak resin is then obtained. However, reaction with epihalohydrin in base may also be carried out in a stepwise fashion whereas first reaction with epihalohydrin is effected followed by reaction of base to form polyepoxide groups of the glycidyl ether composition. Further details concerning the nature of preparation of typical epoxy novolak resins can be obtained in Lee, H. and Neville, K. "Handbook of Epoxy Resins".

A cured epoxy resin may then be prepared in the usual manner by resort to a curing agent such as aliphatic amine of the type set out above.

The amount of curing agent admixture which is employed in curing the epoxy resin compositions here will depend on the amine equivalent weight of the curing agent employed. The total number of equivalents of amine group is preferably from about 0.8 to about 1.2 times the number of epoxide equivalents present in the curable epoxy resin composition with a stoichiometric amount being most preferred.

Various conventionally employed additives can be admixed with these catalyzed polyepoxide-containing compositions prior to final cure. For example, in certain instances it may be desired to add minor amounts of hardeners. Conventional pigments, dyes, fillers, flame-retarding agents and other compatible natural and synthetic resins can also be added. Furthermore, knwon solvents for the polyepoxide materials such as acetone, methylethyl ketone, toluene, benzene, xylene, dioxane, methyl isobutyl ketone, dimethylformamide, ethylene glycol monoethyl ether acetate, and the like, can be used if desired, and where necessary.

The polyepoxide-containing compositions can be used in any of the applications for which polyepoxides are customarily used, e.g., as adhesives, impregnants, surface coatings, potting and encapsulating compositions, in laminates and, particularly, as adhesives for bonding metallic elements or structures together.

The preparation and use of the epoxy resins of this invention will now be further illustrated in the following examples which are for purposes of illustration and should not be considered as a limitation of the scope of the invention.

EXAMPLE I — PREPARATION OF NOVOLAK RESIN

To a 15 gal. kettle was added 24.7 pounds (0.263 lb. moles) of phenol and a solution of 115 g of oxalic acid dihydrate in 2.0 lb. of water. The resulting mixture was heated to 90° C. under nitrogen and 14.2 pounds (0.175 lb. moles) of 37% aqueous formaldehyde was pressured in through the bottom of the kettle over a 15 minute period. After this addition the temperature was raised to 100°–105° C. and held at this temperature for 2 hours. After the digestion the temperature was raised to 180° C. and a water-phenol distillate weighing 14.7 pounds was collected overhead. The distillate contained about 4% phenol.

The novolak resin contained 6.5% free phenol as measured by gel permeation chromatography.

EXAMPLE II — PREPARATION OF EPOXY RESIN FROM NOVOLAK RESIN

| REACTANTS | WT.G. |
|---|---|
| Novolak resin as prepared in Example I | 108 |
| Epichlorohydrin | 694 |
| Sodium Hydroxide (50% in water) | 50 |

The epichlorohydrin and the novolak resin were placed in a one-liter resin flask equipped with a stirrer, thermometer, dropping funnel and azeotroping apparatus for removal of top layer of water and fixed to recycle the lower layer of epichlorohydrin. The mixture was heated to 105° C., base added and held at 95°–120° C. for about 4 hours. 124 g of water was removed by azeotroping. The epichlorohydrin was stripped to a pot temperature of 130° C. The product was cooled and 200 g of toluene was added and this solution was filtered to remove the salts. The filtrate was stripped to a pot temperature of 140° C. to remove the toluene, then further stripped to a pot temperature of 155° C. in 15 min. The product weighted 179 g and was a soft semi-solid. The number of epoxy groups per 100 g of resin was 0.395 or epoxy content of 3.95 meq/g.

EXAMPLE III — CURING OF EPOXY NOVOLAK RESIN WITH POLYAMINE

| REACTANTS | |
|---|---|
| Epoxy resin, prepared in Example II | 100 parts |
| Polyoxypropylenediamine curing agent, M.W. of 400 | 34 parts |

Here the components were mixed with heating and poured into an open-faced mole. The mold was placed in an oven and cured 2 hours at 80° C., and then 3 hours at 150° C. A cured panel was removed from the mold after cooling.

EXAMPLE IV — NOVOLAK COATING

| FORMULATION | |
|---|---|
| Epoxy novolak resin as prepared in Example II | 100 parts |
| Curing agent of Example III | 34 parts |
| Solvent | 100 parts |

The novolak epoxy resin was first dissolved in the solvent to which was then added the curing agent. The reactant solution was then brushed onto a steel panel. The following curing results were obtained:

| Drying Time, 3–4 mil film | |
|---|---|
| Set to touch, hrs. | 3.2 |
| Thru-dry, hrs. | 4.0 |
| Thru-dry, reverse impact, in.-lbs. to fail | |
| Cure: 24 hrs. R.T. | 160 |
| 24 hrs. R.T., 1 hr. 110° C. | 28 |

Jeffamine D-400 Amine obtainable from Jefferson Chemical Co., Inc. Houston, Texas.

Thus, it can be seen that a fast curing coating with good impact properties was obtained with a typical novolak epoxy resin of the invention.

EXAMPLE V — PREPARATION OF NOVOLAK EPOXY RESIN

| REACTANTS | |
|---|---|
| Novolak Resin of Example I | 216 g |
| Epichlorohydrin | 1388 g |
| Sodium Hydroxide | 100 g in 200 g water |

Another useful novolak epoxy resin was prepared similar to that of Example II. The epichlorohydrin and novolak were placed in a 2 liter flask equipped with a stirrer, thermometer, dropping funnel and azeotroping apparatus for removal of top layer of water and recycle of the lower layer of epichlorohydrin. The contents were heated to 104° C. and addition of aqueous sodium hydroxide started. The caustic was added over a period of 30 minutes and the contents heated fro about 5 hours at 94°–118° C. During this period 240 g of water was removed. The contents were further heated to 148° C. to remove the excess eipchlorohydrin. Then 300 ml of toluene was added and the salt was filtered. Since the product did not seem completely soluble in toluene, small amounts of n-butanol and ethylene glycol monoethane ether was added. The solvents were stripped to 180° C. at 5 mm. The novolak epoxy resin product weighed 311 g and represents a yield of 94.3%.

While the invention has been explained in relation to its preferred embodiment, it is to be understood that various modifications thereof will become apparent to those skilled in the art upon reading the specification and is intended to cover such modifications as fall within the scope of the appended claims.

We claim:
1. A glycidyl ether composition useful as an epoxy resin which comprises the reaction product of an epihalohydrin and a novolak resin containing 5–25 weight percent of phenol or substituted phenol based on the weight of said novolak resin said phenol or substituted phenol having the structure:

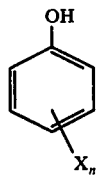

wherein X is hydrogen, hydroxy, chlorine, bromine or an alkyl radical having from 1 to 12 carbon atoms; $n$ is an integer from 1 to 2.

2. The composition of claim 1 wherein said epihalohydrin is epichlorohydrin.
3. The composition of claim 1 wherein said novolak resin containing said phenol or substituted phenol is prepared by reacting 1.5–3.0 moles of phenol or substituted phenol per mole of formaldehyde.
4. An epoxy resin prepared by reacting the glycidyl ether composition of claim 1 with a base.
5. A cured epoxy resin prepared by curing the epoxy resin of claim 4 with a curing agent.
6. A process for preparing a glycidyl ether composition useful as an epoxy resin which comprises reacting an epihalohydrin and a novolak resin containing 5–25 weight percent of phenol or substituted phenol based on the weight of said novolak resin, and recovering said glycidyl ether composition from the reaction mixture said phenol or substituted phenol having the structure:

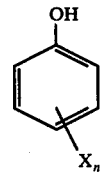

wherein X is hydrogen, hydroxy, chlorine, bromine or an alkyl radical having from 1 to 12 carbon atoms, $n$ is an integer from 1 to 2.